(12) United States Patent
Cunningham

(10) Patent No.: US 9,668,675 B2
(45) Date of Patent: *Jun. 6, 2017

(54) SENSING DEVICE

(71) Applicant: Thomas J. Cunningham, Smyrna, GA (US)

(72) Inventor: Thomas J. Cunningham, Smyrna, GA (US)

(73) Assignee: Thomas J. Cunningham, Smyrna, GA (US)

( * ) Notice: Subject to any disclaimer, the term of this patent is extended or adjusted under 35 U.S.C. 154(b) by 278 days.

This patent is subject to a terminal disclaimer.

(21) Appl. No.: 14/529,391

(22) Filed: Oct. 31, 2014

(65) Prior Publication Data

US 2015/0051515 A1 Feb. 19, 2015

Related U.S. Application Data

(63) Continuation of application No. 13/087,894, filed on Apr. 15, 2011, now Pat. No. 8,880,358.

(60) Provisional application No. 61/325,078, filed on Apr. 16, 2010.

(51) Int. Cl.
| | |
|---|---|
| *A61B 5/11* | (2006.01) |
| *G01L 1/00* | (2006.01) |
| *G06F 17/40* | (2006.01) |
| *G06F 19/00* | (2011.01) |
| *A61B 5/00* | (2006.01) |
| *A61B 5/107* | (2006.01) |

(52) U.S. Cl.
CPC .............. *A61B 5/1116* (2013.01); *A61B 5/11* (2013.01); *A61B 5/1121* (2013.01); *A61B 5/4528* (2013.01); *G01L 1/00* (2013.01); *A61B 5/1071* (2013.01); *A61B 5/6806* (2013.01); *A61B 5/6826* (2013.01); *A61B 5/6828* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 3,285,070 A | * | 11/1966 | McDonough | A61B 5/1107 482/115 |
| 4,436,099 A | * | 3/1984 | Raftopoulos | A61B 5/1071 600/587 |
| 7,762,145 B2 | * | 7/2010 | Bechtold | G01M 13/027 73/760 |

(Continued)

*Primary Examiner* — Edward Cosimano
(74) *Attorney, Agent, or Firm* — Quinn IP Law

(57) ABSTRACT

A sensing device including a sensor, a triggering mechanism is provided. The sensing device is attachable to a covering positioned in contact with a body such that the triggering mechanism extends between first and second segments of the body. Movement of at least one of the first and second segments activates the triggering mechanism to provide an input to the sensor, actuating the sensor to generate an output defining at least one measurement of the movement. The measurement may be one or more of rotation, translation, velocity, acceleration, and joint angle. An intermediate mechanism may be interposed between the triggering mechanism and the sensor. The sensing device may include a means to process or record measurements corresponding to movement. A system and method of measuring the movement is also provided.

25 Claims, 5 Drawing Sheets

(56) References Cited

U.S. PATENT DOCUMENTS

| | | | |
|---|---|---|---|
| 8,880,358 B2* | 11/2014 | Cunningham | A61B 5/1116 600/595 |
| 8,961,439 B2* | 2/2015 | Yang | A61B 5/1038 600/595 |
| 2008/0276721 A1* | 11/2008 | Bechtold | G01M 13/027 73/849 |
| 2011/0257928 A1* | 10/2011 | Cunningham | A61B 5/1116 702/150 |
| 2012/0253234 A1* | 10/2012 | Yang | A61B 5/1038 600/595 |

* cited by examiner

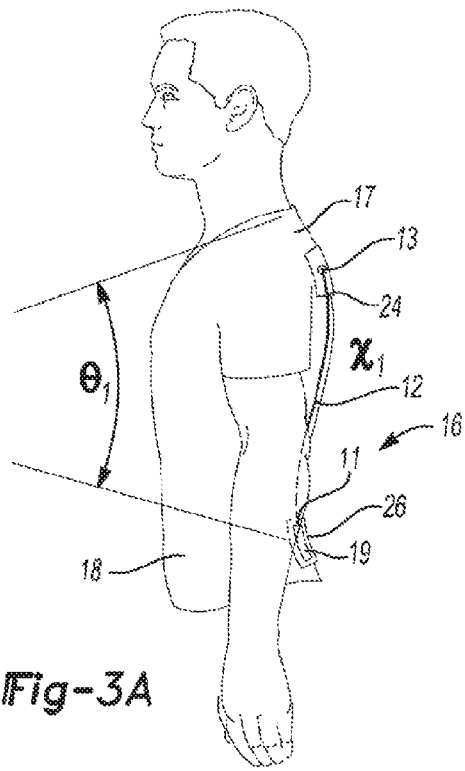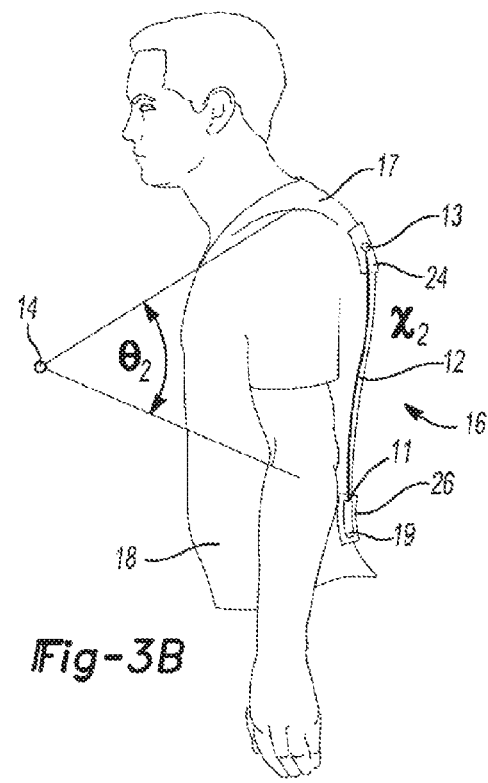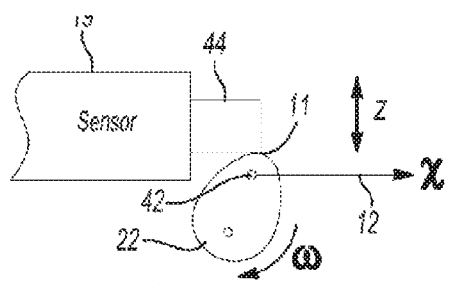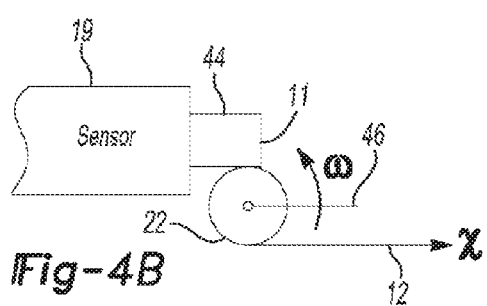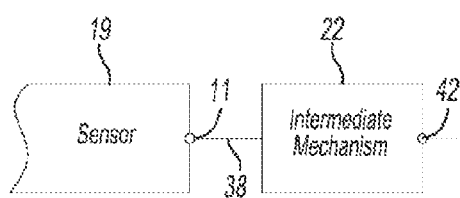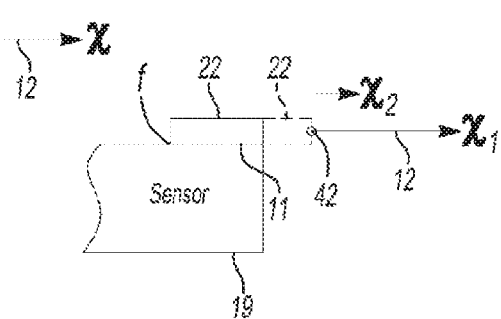

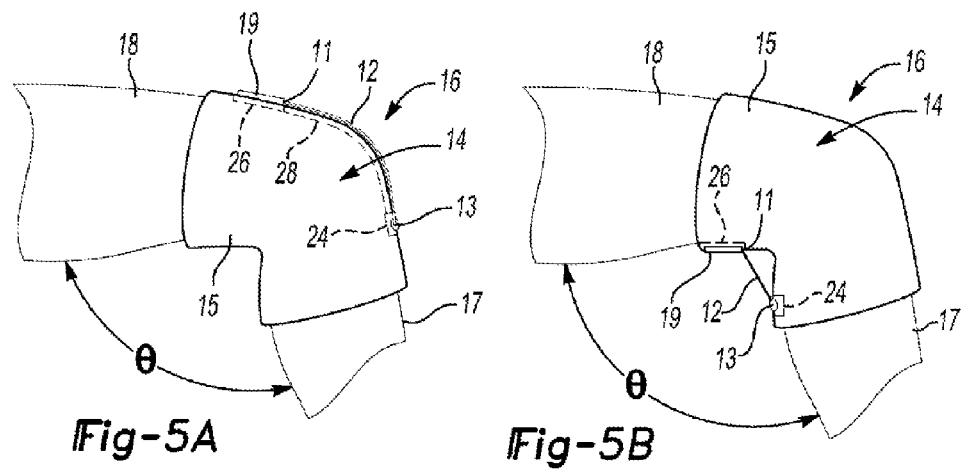
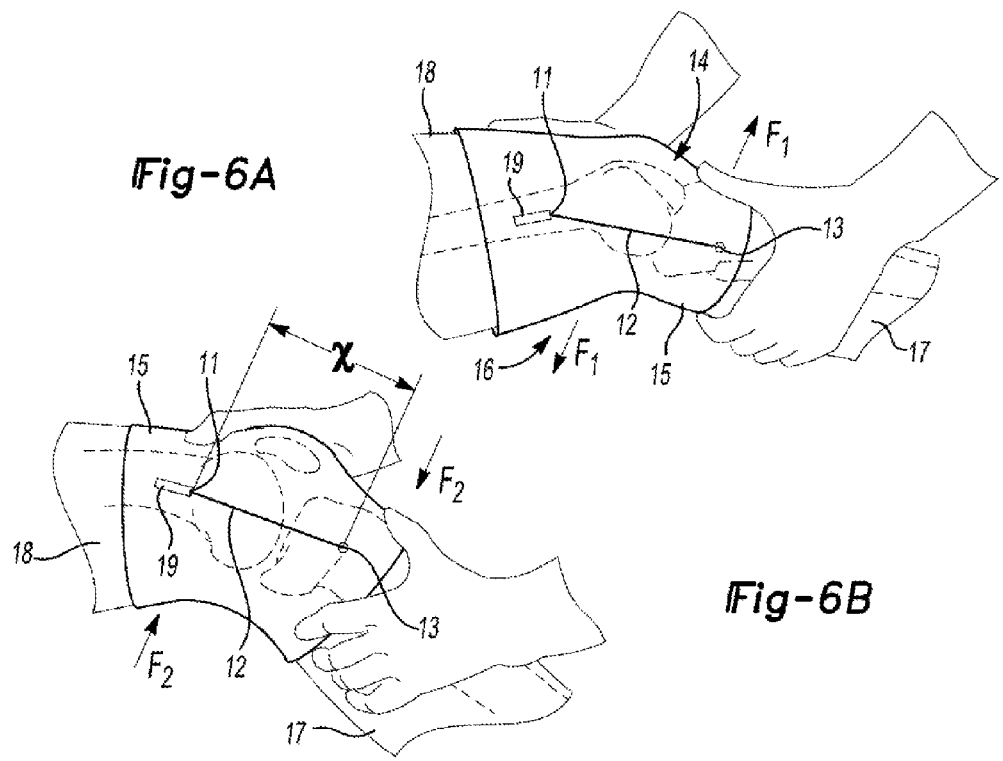
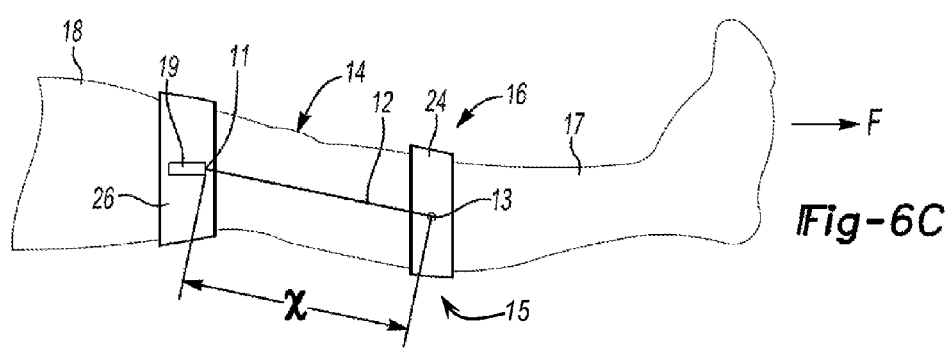

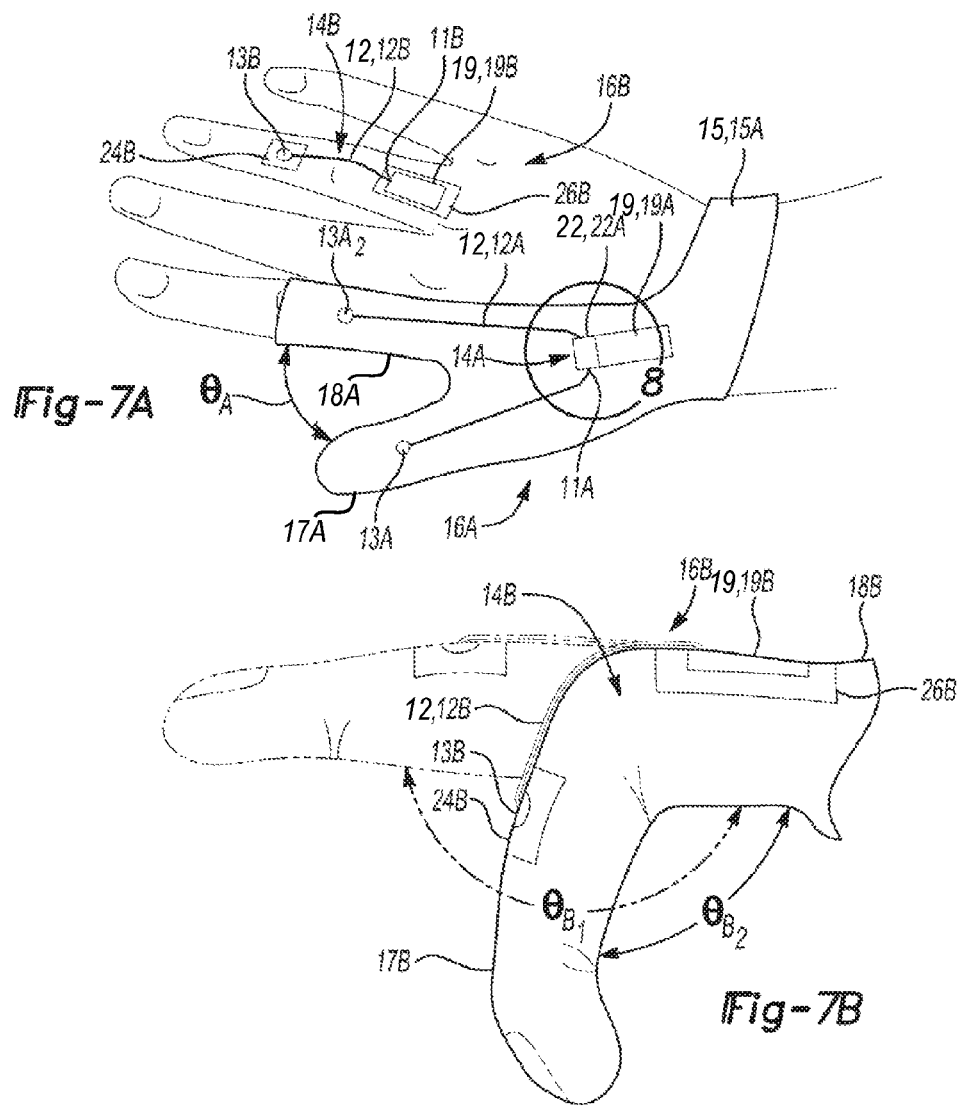
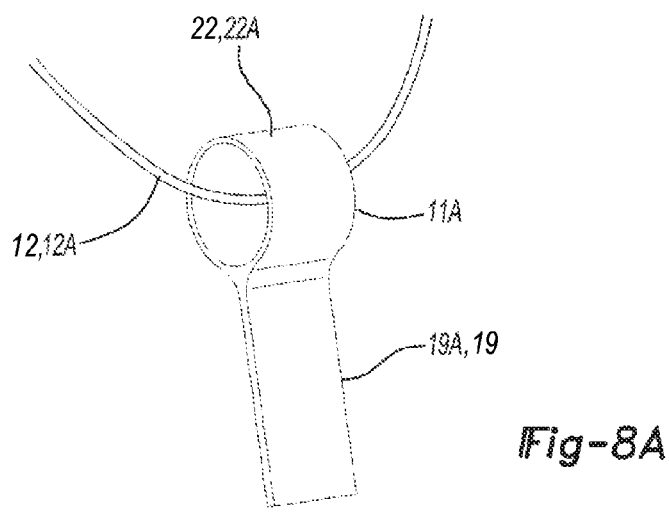

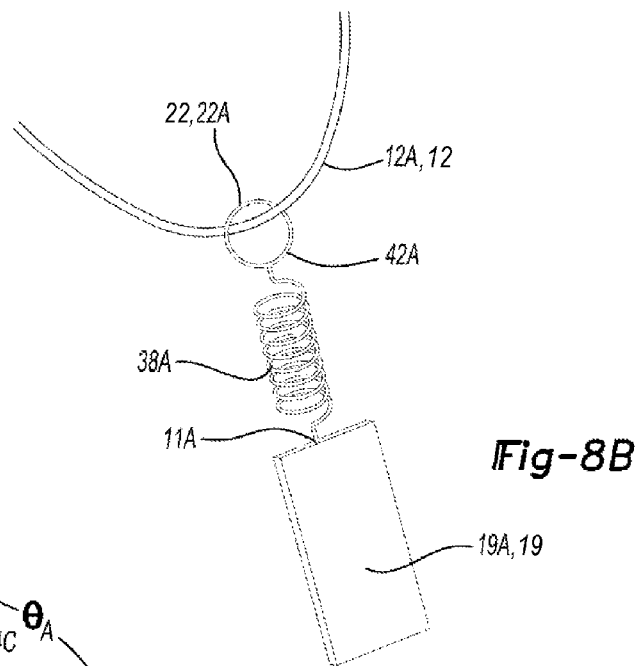
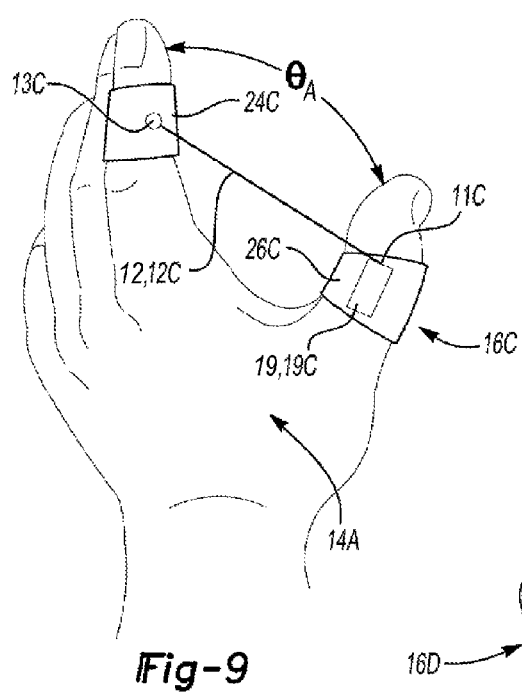
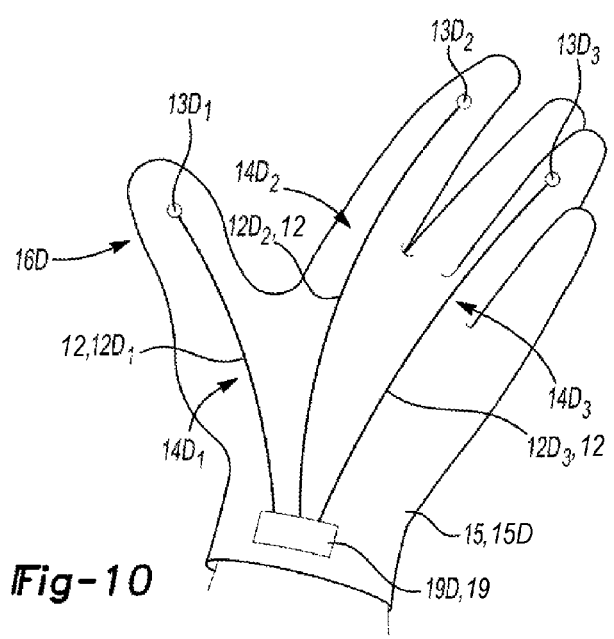

SENSING DEVICE

CROSS-REFERENCE TO RELATED APPLICATIONS

This application claims the benefit of U.S. patent application Ser. No. 13/087,894 filed on Apr. 15, 2011 now U.S. Pat. No. 8,880,358 and U.S. Provisional Patent Application No. 61/325,078 filed on Apr. 16, 2010, which are hereby incorporated by reference in their entirety.

TECHNICAL FIELD

The present invention relates to the field of biomechanics and more specifically to measurement of movements of body segments.

BACKGROUND

The performance of a skilled task requires coordinated intra-limb and inter-limb movement patterns. Performing a task a multitude of times or deviating from a specific coordinated pattern can result in an undesirable task being performed or an injury to the performer. Deviation from a desired coordination pattern can be the result of many factors including, but not limited to, performer fatigue, the skill level of the performer, difficulty of the desired task or changing environmental conditions. Knowledge relating to the position of the joints during the performance of a task can be beneficial to identify and classify patterns of movement inherent in particular tasks. When patterns of movement are identified, it is similarly desirable to identify when a particular movement has occurred, how many times that movement has occurred and several other characteristics that can describe the particular motion.

Observation, assessment and interpretation of movements are routinely used by coaches, therapists, clinicians, ergonomics engineers and biomechanists to identify patterns in joint movements. This process can be subjective and generally relies on the skill of the observer to identify relationships in joint movements, to distinguish between changes in movements and to count the amount of movements performed. Using subjective measures by an observer introduces accuracy, repeatability and validity concerns when evaluating limb movements. Further, subjective measures can be difficult to implement due to costs associated with observation time.

Instrumentation of limbs to objectively observe motions is currently used to address some of the above mentioned limitations; however, instrumentation of the limbs has limitations. For example, current methods of instrumentation of limbs can be obtrusive to the performer, costly to implement and can seldom be readily used outside a laboratory condition in a reliable manner.

SUMMARY

A sensing device and system for measuring movement of a moving segment of a body relative to a reference segment of the body is provided. The sensing device includes a covering configured to be positioned in contact with a body, the covering including a first covering portion and a second covering portion. The first covering portion is configured to be positioned in contact with a moving segment of a body, and the second covering portion is configured to be positioned in contact with a reference segment of the body. The sensing device further includes a sensor operatively attached to the second covering portion, and a triggering mechanism operatively attached at a first end to the first covering portion and operatively connected at a second end to the sensor. The triggering mechanism extends from the moving segment to the reference segment and across a joint center located between the moving segment and the reference segment when the covering is positioned in contact with the body. The sensing device is configured such that when the covering is positioned in contact with the body, movement of the moving segment activates the triggering mechanism to provide a force input to the sensor. The force input actuates the sensor to generate an output defining at least one measurement of the movement of the moving segment.

The sensing device may further include a processor configured to receive and process the output. By way of non-limiting example, the sensing device may be configured to be in contact with a body where the moving segment is one of adjacent or non-adjacent to the reference segment, and/or one of contralateral or ipsilateral to the reference segment, and/or one of proximal or distal to the joint center between the moving segment and the reference segment. The sensing device may be configured to measure one or more of a joint angle, a translation distance, a movement velocity, a movement acceleration, and a count of the number of repetitions of the movement. The sensing device may include a removable storage device configured to receive the output from the sensor such that the output can be transferred to a remote device. In a non-limiting example, the sensing device may be configured for wireless communication with a remote device such that the output can be transferred wirelessly to the remote device.

In an optional configuration, an intermediate mechanism may be operatively attached to the second end of the triggering mechanism and configured to be in selective communication with the sensor, such that movement of the moving segment activates the triggering mechanism to provide a force input to the intermediate mechanism. The intermediate mechanism may be configured to transfer the force input from the sensor when the force input meets a predetermined threshold, and to isolate the force input from the sensor when the force input does not meet the predetermined threshold.

The system for measuring movement of a moving segment of a body relative to a reference segment of the body includes a sensing device for measuring the movement, and may additionally include a processor, and one or more of an output device, a storage device, and a computing device in communication with the sensing device and/or processor. The system may be configured with a plurality of sensing devices, sensors and/or triggering mechanisms. A method for measuring movement of a moving segment of a body is also provided.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 3A is a schematic view of a body in contact with a sensing device configured to measure a joint angle defined by non-adjacent segments, the body in a position corresponding to a first joint angle;

FIG. 3B is a schematic view of the body and sensing device of FIG. 3A, the body in a position corresponding to a second joint angle;

FIG. 4A is a schematic partial view of the sensing device of FIG. 1, including a connector in a first configuration;

FIG. 4B is a schematic partial view of the sensing device of FIG. 1, including a connector in a second configuration;

FIG. 4C is a schematic partial view of the sensing device of FIG. 1, including a connector in a third configuration;

FIG. 4D is a schematic partial view of the sensing device of FIG. 1, including a connector in a fourth configuration;

FIG. 5A is a schematic view of a knee joint and a sensing device including a triggering mechanism integrated into the covering of the sensing device and configured to measure rotation of the knee joint;

FIG. 5B is a schematic view of a knee joint and a sensing device including a triggering mechanism attached to the covering of the sensing device;

FIG. 6A is a schematic view of a knee joint in a first position and in contact with a sensing device configured to measure translation of the knee joint;

FIG. 6B is a schematic view of the sensing device and knee joint of FIG. 6A, the knee joint translated to a second position;

FIG. 6C is a schematic view of a knee joint and a sensing device, the sensing device including a plurality of covering portions and configured to measure translation of the knee joint;

FIG. 7A is a schematic plan view of a hand in contact with a plurality of sensing devices;

FIG. 7B is a schematic partial view of a portion of the hand of FIG. 7A, with the finger joint including the sensing device in a second position;

FIG. 8A is a schematic partial view of a sensing device of FIG. 7 showing the connector in additional detail;

FIG. 8B is a schematic partial view of the sensing device of FIG. 7 showing an alternative configuration of the connector including an intermediary triggering mechanism; and FIG. 9 is a schematic view of a hand in contact with a sensing device; and FIG. 10 is a schematic view of a hand in contact with a sensing device, the sensing device including a plurality of triggering mechanisms.

DETAILED DESCRIPTION

Provided herein is a sensing device including a covering, which may be used to instrument a body to measure movement of a limb, segment or joint center of the body. A system including the sensing device is provided, and shown schematically in FIG. 1. A plurality or combinations of sensing devices may be configured in a covering to measure the movement of a combination of the limbs, segments and joint centers which are in contact with the covering. Alternately, a combination of sensing devices may be used in combination and the measurements obtained therefrom analyzed in combination to monitor and/or determine patterns of movement of a body.

Figure 1:
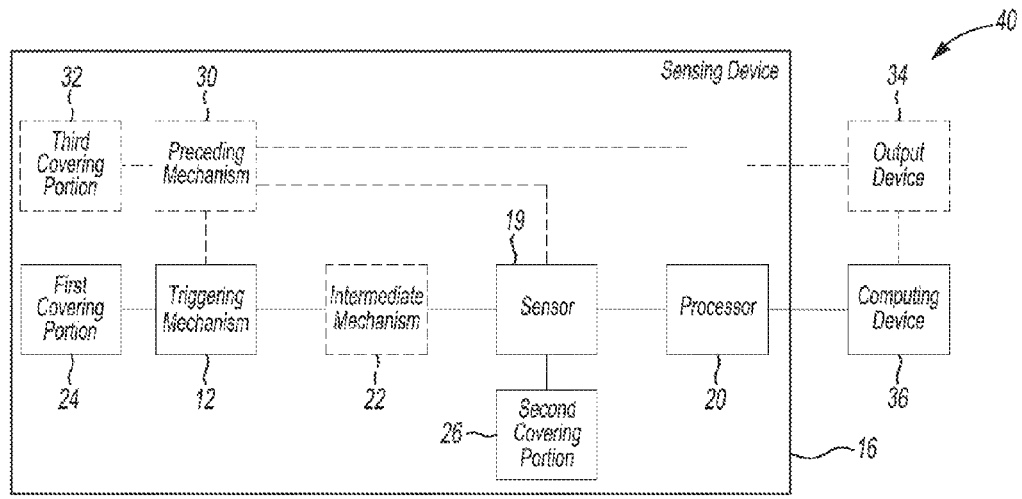
FIG. 1 is a schematic illustration of a system including a sensing device.
Figure 2A:
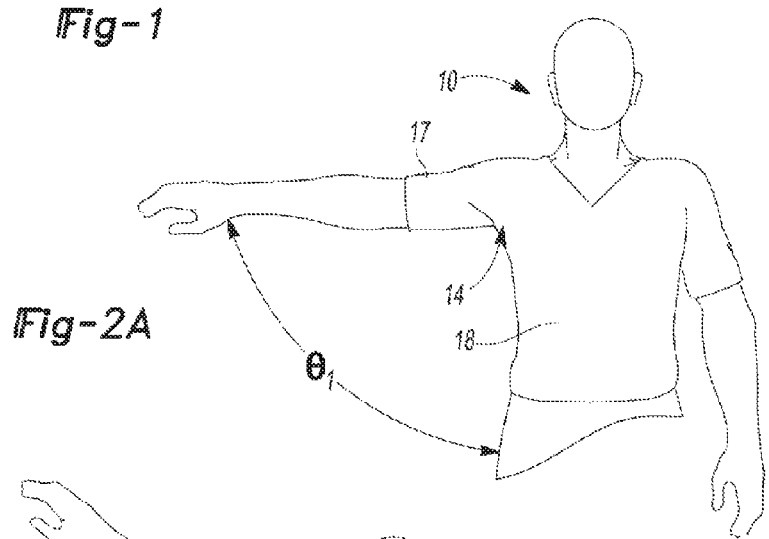
FIG. 2A is a schematic view of a body including a body segment in a position corresponding to a first joint angle and in contact with the covering shown in further detail in FIG. 2B.
Figure 2B:
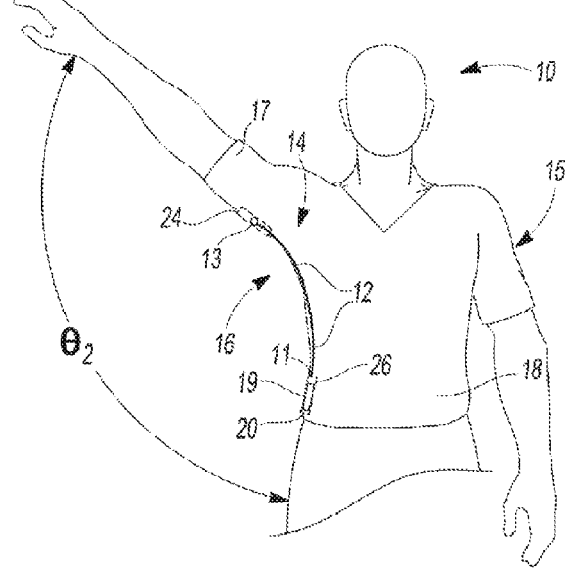
FIG. 2B is a schematic view of the body of FIG. 2A with the body segment in a position corresponding to a second joint angle, and the sensing device of FIG. 1 including the covering of FIG. 2.

Referring now to FIGS. 1, 2A and 2B, shown generally at 40 is an example system including a sensing device 16. As shown in FIG. 1 and in a non-limiting example in FIG. 2B, the sensing device 16 includes a sensor 19 and a triggering mechanism 12, which are each operatively attached to a covering 15. The covering 15 includes a first covering portion 24 and a second covering portion 26. The covering 15 is shown, by way of example, configured as a covering 15A in FIG. 7A, and as a covering 15D in FIG. 10. The sensing device 16 is configured such that the first covering portion 24 may be positioned in contact with a moving segment 17 of a body 10, and such that the second covering portion 26 may be positioned in contact with a reference segment 18 of the body 10. The sensor 19 is operatively attached to the second covering portion 26, and is operatively connected to a first end of the triggering mechanism 12 at an attachment or input interface 11. The sensor 19 is shown, by way of example, configured as a sensor 19A in FIGS. 7A, 8A and 8B, as a sensor 19B in FIGS. 7A and 7B, as a sensor 19C in FIG. 9, and as a sensor 19D in FIG. 10. The triggering mechanism 12 may be made of an elastic material, which may be configured as an elastic cord, band, strap or segment or other material or of another configuration capable of exerting a force input, e.g., a load on the sensor 19 when activated by a movement of the body 10. The second end of the triggering mechanism 12 is operatively connected to the input interface 11 of the sensor 19 by one or more of stitching, sewing, gluing, clamping, knitting, clipping, snapping, or otherwise operatively affixing the second end of the triggering mechanism 12 to the sensor 19. The triggering mechanism 12 is shown, by way of example, configured as a triggering mechanism 12A in FIGS. 7A, 8A and 8B, as a triggering mechanism 12B in FIGS. 7A and 7B, as a triggering mechanism 12C in FIG. 9, and as triggering mechanisms $12D_1$, $12D_2$, and $12D_3$ in FIG. 10. The direction of the force input exerted by the triggering mechanism 12 on the input interface 11 of the sensor 19 may vary with the configuration of the sensing device 16. In the examples described herein, the force input is typically configured as a tensile load exerted on the sensor 19, however these examples are not intended to be limiting.

The triggering mechanism 12 is attached at the second end to the first covering portion 24 at an attachment 13, such that when the covering 15 is positioned in contact with the body 10, the elastic material of the triggering mechanism 12 extends from the first covering portion 24 in contact with the moving body segment 17 to the sensor 19 attached to the second covering portion 26 in contact with the reference body segment 18, and across a joint center 14 located between the moving body segment 17 and the reference body segment 18. The attachment 13 of the end of the triggering mechanism 12 to the covering 15 may be made by one or more of stitching, sewing, gluing, clamping, knitting, clipping and snapping or otherwise affixing the first end of triggering mechanism 12 to the first portion 24 of the covering 15. The elastic material triggering mechanism 12 and the sensor 19 are configured such that, when a performer (shown in FIG. 2A as the body 10) wearing the sensing device 16 moves, the covering 15, including the first and second portions of the covering 24, 26, moves with the moving body segment 17 and relative to the reference body segment 18 to activate the triggering mechanism 12. The sensing device 16 may be configured such that when the joint angle θ (see FIGS. 2A and 2B) is at its minimum, the triggering mechanism 12 is preloaded to provide a preload force to the sensor 19. For the example shown in FIG. 2B, the preload would be configured as a minimal tensile load on sensor 19 when θ approaches zero degrees (not shown). The activated triggering mechanism 12 exerts a force on the sensor 19, which actuates the sensor 19 causing the sensor 19 to generate a signal corresponding to the movement of the moving segment 17 and, in the example shown in FIGS. 2A-2B, corresponding to changes in the joint angle θ defined by the moving body segment 17, the reference body segment 18 and the joint 14 located therebetween.

The sensor 19 may include one or a combination of an accelerometer, a piezoelectric crystal, a piezoelectric film, a piezo-resistive film, a strain gauge or a similar sensing mechanism capable of converting an input load into an output signal. The output signal may be used to measure the movement of the moving segment 17 relative to the reference segment 18, to derive a translation distance, to derive the joint angle of a joint included between the segments 17, 18, and/or to derive a velocity of the movement, and or/or derive an acceleration of the movement. A plurality of output signals, each corresponding to a movement, may be collected, logged and/or stored, and/or used to analyze patterns of movement and/or to count the number of repetitions of a movement. As described previously, the sensor 19 may be operatively attached to a second portion 26 of the covering 15 in contact with the reference body segment 18. Alternatively, the sensor 19 may be configured such that sensor 19 is connected or mounted to a circuit board, or may be integrated with a means for signal processing, such as a processor 20, or with a storage device, which may be configured as a removable memory device, or a combination of these. In such a configuration, for example, sensor 19 may be operatively attached to covering 15 by attaching the circuit board, processor, storage device or other mechanism with which sensor 19 is integrated or connected to the covering 15.

Referring to FIG. 2A, shown generally at 10 is a body, which may also be referred to herein as a performer or a wearer, including a moving body segment 17, a reference body segment 18 and a joint center 14. The moving body segment 17 may also be referred to as the first body segment or the moving segment. The reference body segment 18 may also be referred to as the second body segment or the reference segment. For illustrative purposes and by way of non-limiting example, in FIGS. 2A and 2B the moving body segment 17 is an arm, the reference body segment 18 is a torso, and the joint 14 located between moving body segment 17 and adjacent body segment 18 is a shoulder joint 14. The position of the arm 17 relative to the torso 18, and the shoulder joint 14 define a joint angle indicated as θ, the endpoint of which is the center of shoulder joint 14. A sensing device 16, shown in FIG. 2B, is configured to measure the actions and movements of moving segment 17 relative to the shoulder joint generally indicated at 14 and relative to the reference segment 18.

As the moving segment 17 is moved, at least a portion of the covering 15, including the first covering portion 24 moves with the moving segment 17, activating the triggering mechanism 12 and causing triggering mechanism 12, which in the example provided is an elastic band or cord, to stretch and contract corresponding to movements of moving segment 17, thus imparting various loads on sensor 19 as moving segment 17 moves. The triggering mechanism 12 is typically configured to exert a tensile load on the sensor 19, where changes in the tensile load correspond to movement of the moving body segment 17, such as the movement from a first joint angle $\theta_1$ corresponding to a first position of the moving segment 17 shown in FIG. 2A to a second joint angle $\theta_2$ corresponding to a second position of the moving segment 17 shown in FIG. 2B.

The sensing device 16 may be configured such that the triggering mechanism 12 provides a force input directly to the sensor 19, as shown in FIG. 2B. In an optional configuration, the sensing device 16 may include an intermediate mechanism 22 (see FIGS. 1, 4A-4D and 8A-8B) interposed between the triggering mechanism 12 and the sensor 19, which may be configured with a cam-type mechanism, electronic circuitry, or another mechanism, such that input forces (loads) generated by the triggering mechanism 12 which do not meet a predetermined threshold are filtered or isolated from the sensor 19 so as not to produce a signal or sensor response. As will be described in further detail, the intermediate mechanism 22 is configured such that an input force generated by the triggering mechanism 12 which does meet the predetermined threshold is transferred or otherwise transmitted via the intermediate mechanism 22 to the input interface 11 of the sensor 19.

Referring to FIGS. 2A and 2B, when movement of the moving segment 17 occurs, such as the movement of arm 17 and shoulder joint 14 from the position shown in FIG. 2A to the position shown in FIG. 2B, the joint angle θ of joint center 14 is altered from $\theta_1$ to $\theta_2$ and the length of elastic material of triggering mechanism 12 changes, altering the tensile force applied in the material of the triggering mechanism 12 consistent with Hooke's Law. Alternatively, referring now to FIGS. 6A and 6B, when movement of a moving segment 17 occurs, such as the movement of the moving segment (lower leg) 17 relative to the reference segment (upper leg) 18 and movement of the knee joint 14 from the position shown in FIG. 6A to the position shown in FIG. 6B, the joint position of the joint center 14 is altered such that the length X of the elastic material comprising the triggering mechanism 12 changes, altering the tensile force applied to the sensor 19. Changes in joint angle θ(t) and changes in the translation distance T(t) correspond to changes in length X(t) of the elastic material of the triggering mechanism 12 which correspond to changes in force F(t) applied to the sensor 19. The change in force F(t) corresponds to a change in voltage output V(t) from the sensor 19 producing the relationship modeled in equation (1), assuming the triggering mechanism 12 has a spring coefficient k.

$$kT(t)+k\theta(t) \cong kX(t) \cong F(t) \cong V(t) \quad (1)$$

When an intermediate mechanism 22 is interposed between the triggering mechanism 12 and the input interface 11 of the sensor 19, as described herein, the intermediate mechanism 22 produces a force F(s) on the sensor 19 which correspond to a change in voltage output V(t) from the sensor 19 which can be modeled by equation (2), assuming the triggering mechanism 12 has a spring coefficient k.

$$kT(t)+k\theta(t) \cong kx(t) \cong F(t) \rightarrow F(s) \rightarrow V(t) \quad (2)$$

Additionally, it should be recognized that the use of the above mentioned sensor 19 attached to the covering 15 about a moving segment 17 can produce a signal independent of a triggering mechanism 12 which might also be useful in analysis of the joint movement in question.

Referring again to FIG. 1, the system 40 may include a processor 20, an optional output device 34, and a computing device 36. It would be understood that one or more of these devices 20, 34, 36 may be configured to perform some or all of the functions of one or more of the other devices, and that the system 40 configured as illustrated by FIG. 1 is not intended to be limiting. For example, the computing device

36 may be configured to perform some or all of the output and processing functions of the output device 34 and the processor 20, respectively. One or more of the output device 34, the computing device 36, and the processor 20, may be referred to herein as a remote device, when the device is so configured as remote from the sensing device 16 within the system 40, e.g., when device which is not physically connected to the sensing device 16 by wiring, cables, or other physical means.

The system 40 may include a storage device (not shown) which may be configured to include, by way of example, Read Only Memory (ROM), Random Access Memory (RAM), electrically-erasable programmable read only memory (EEPROM), etc., of a size and speed sufficient for logging and storing the output signals and measurements generated by the sensing device 16, and as required, for performing analysis of the logged and/or stored information using the processor 20 and/or the computing device 36. One or more of the sensing device 16, the processor 20, the output device 34 and the computing device 36 may be configured as or to include a storage device or memory.

By way of non-limiting example, the storage device may be configured as a USB, a USB cable, a flash drive, a memory chip, or other removable memory device. The sensing device 16 may be configured in communication with the removable storage device such that output signals and/or measurements may be received, stored and/or logged to the removable memory device during actuation of the sensor 19 by a movement of the body 10 activating the triggering device 12. The removable storage device may be removed from the sensing device 16 and placed in communication with one or more remote devices, such that storage and transfer of the information (signals, measurements) logged and/or output from the sensing device 16 to the remote device for storage, display, analysis, etc. can easily occur.

In another non-limiting example, the sensing device 16 may be configured for contactless or wireless communication with a remote device, using BLUETOOTH®, Radio Frequency Identification (RFID), Wi-Fi™, or any other near field communication means. The sensing device 16 may be configured such that the output signal from the sensor 19 and/or measurement derived therefrom is transmitted to one or more remote devices in real time, e.g., as the output signal is generated by actuation of the sensor 19 caused by activation of the triggering mechanism 12 by movement of the moving segment 17. The sensing device 16 may be configured to receive signals and/or information transmitted wirelessly from a remote device to the sensing device 16.

The output device 34 may be configured to display the signal and/or the measurement generated by the sensing device 16, a plurality of signals and/or measurements logged and/or stored within the system 40, a count of the movements or repetitions thereof measured by the sensing device 16, results of analysis of the logged data, which may include identification and analysis of patterns of movement, etc. The output device 34 may be configured to display the information as described previously, and/or may be configured to display messages and/or alerts. The output device 34 may be configured to provide output configured as one or a combination of an audio output, a visual output, an audio-visual output, an electronic output, and a printed output. The output may be provided as a message or alert, for example, to the wearer of the sensing device 16, to notify the wearer 10 of information related to the wearer's movements as measured by the sensing device 16 or to communicate status relative to a predetermined rule, threshold or condition corresponding to the wearer's movements, as measured by the sensing device 16, to the wearer. Non-limiting examples of messages or alerts which may be provided to a wearer 10 may include feedback related to proper and improper movements (magnitude, direction, velocity) or deviation from a specified or desired coordination pattern while performing a task, a therapy or a treatment, etc., a message that a threshold or target count has been met for a repetitive movement, an alert that a recommended movement limit is being approached or has been exceeded, etc.

The computing device 36 may be configured to store and/or analyze the signals and/or measurements generated by the sensing device 16. The computing device 36 may be configured to, by way of example, analyze the movements corresponding to the signals and/or measurements, to identify patterns of movements, to count repetitions of movements, to generate messages, alerts, reports and/or other forms of output based on the information generated by and/or obtained from the sensing device 16. In a non-limiting example, information (signals, measurements) may be collected from a wearer 10 configured with one or more sensing devices 16 during performance of a particular task, to identify and classify patterns of movement inherent in the particular tasks. Analysis of the patterns of movement may be used to redesign the task or environment within which the task is performed, to develop training of an optimized method or sequence for performing the task, etc.

The processor 20 may be configured to receive and process the output signals and/or measurements generated by the sensor 19 and/or sensing device 16. The processor 20 may also be configured as and/or referred to, by way of non-limiting example, as a circuit, a circuit board, a conditioning circuit, a signal processor, or a printed circuit board assembly (PCBA). The processor 20 may be configured to process the output signals and/or measurements defined by the output signals by one or more of filtering, amplifying, counting, transmitting, converting (for example, from analog to digital), recording, and storing the output signals and/or measurements. The processor 20 may be operatively connected to the sensor 19 and/or the sensing device 16 (see FIG. 2B), or may be configured as a remote device which may be in wireless communication with the sensing device 16 (as described for FIGS. 3A-3B).

The sensing device 16 may include a plurality of sensors 19 and/or triggering mechanisms 12, wherein one or more of the triggering mechanisms 12 may be configured to exert an input force on one or more sensors 19, and one or more sensors 19 may be in communication with a processor 20. The distance between the processor and one or more sensors operatively connected to the processor may be varied, for example, by using sensor leads, wires, and/or cables of variable length, or other connecting means to facilitate placement and attachment of the processor 20 to another portion of the covering 15 other than the second portion 26 and/or adjacent to or directly connected to the sensor 16, or as required to configure the processor 20 to receive and process signal outputs from a plurality of sensing devices 16 and/or sensors 19 operatively attached to the covering 15.

Other measures, such as the velocity or acceleration of a signal, which may correspond to the velocity or acceleration of a movement, may be monitored. Threshold values can be established for measures, such that only values meeting the threshold values are recorded, for example, to eliminate signal values associated with incidental or non-studied movements or signal noise. The threshold value may be a value which must be exceeded or alternatively, a threshold value may be a value which must not be exceeded, depending on the objective of the measurement or monitoring study.

Mechanical or electrical means may be provided to isolate or filter signal values which do not meet an established threshold level, where the threshold level may be defined as either a minimum or maximum value to be met. Signal values may be isolated or filtered, for example, using the processor 20. As another example, an intermediate mechanism 22, as will be described in further detail, may be used to isolate or filter force inputs from a triggering mechanism 12. As shown in FIG. 1, a preceding mechanism 30 may be configured in operative communication to at least one of the triggering mechanism 12, the sensor 19 and the processor 20, wherein the preceding mechanism 30 may be configured to provide a signal output or actuating input at a threshold level as a prerequisite to activating the triggering mechanism 12, generating an output signal from sensor 19, and/or processing a signal or measurement using the processor 20. As illustrated by FIG. 1, the preceding mechanism 30 may be, for example, operatively attached to a third covering portion 32, where the third covering portion 32 is configured to be in contact with a portion of the body 10. The third covering portion 32 may be in contact with another body segment, e.g., a body segment other than the moving segment 17 or reference segment 18, a joint which may be the joint center 14 or another joint, or another portion of the body 10. The preceding mechanism 30 may be configured similarly to one of a triggering mechanism 12, an intermediate mechanism 22, or of another configuration. For example, the preceding mechanism 30 may include a conductive textile, which may be integrated into the covering 15, and configured to provide a threshold voltage to one of the sensor 19 and the processor 20 as a prerequisite to the sensor 19 generating an output signal, or as a filtering input to the processor 20. Dependent measures collected from the sensor output signals can be transferred or transmitted to the computing device 36 or to another remote device for analysis through several means.

As referred to herein, a body segment, as that term is generally used, and including but is not limited to a moving body segment 17 and a reference body segment 18, refers to a portion (segment) of the body such as a head, torso, arm, forearm, hand, thigh, leg, or foot of the body 10. A body segment may be comprised of a bone or a combination of bones, where the combination of bones may define a body segment. For example, the upper leg may be, by itself, a body segment. As another example, the leg, e.g., the combination of the upper leg and the lower leg, may define a body segment. As another example, and referring generally now to a hand, a first segment may be defined by a metacarpal connecting the wrist bones to a particular finger, and a second segment may be defined by one of or a combination of the phalanges forming that particular finger. In yet another example, a singular vertebra may comprise a body segment, and a portion of the spine including a plurality of vertebrae may comprise another body segment. The term body segment or segment, as used herein, is not intended to be limiting, and may be used to refer to any portion of the body which includes a joint center between that portion of the body and another segment of the body. The sensing device 16 may be configured such that the first covering portion 24 may be positioned in contact with a moving segment 17 and the second covering portion 26 may be positioned in contact with a reference segment 18 wherein the moving segment 17 and the reference segment 18 may be one of adjacent and non-adjacent to each other.

As referred to herein, a joint center refers to the center of a joint of the body 10 which may be located between two adjacent or non-adjacent body segments. Joint centers located between adjacent body segments may include, for example, the joint centers commonly known as the shoulder, elbow, wrist, trunk, neck, hip, knee, and ankle. The term joint center, as used herein, is not intended to be limiting, and may be used to reference the center of a singular joint, such as a hip joint, or may be used to reference the center of a combination of joints, for example, the center of a plurality of vertebrae. A joint center defined by non-adjacent body segments may contain the adjacent segments and their respective joint centers located between the non-adjacent body segments.

A joint angle, as referred to herein, is the angle defined by two adjacent or non-adjacent body segments and a joint center between the body segments, where the endpoint of the angle corresponds with the joint origin. For example, a joint angle may be defined by the upper arm segment, forearm and elbow, where the endpoint of the joint angle coincides with the elbow joint and the upper arm and forearm are adjacent body segments. As another example, a joint angle may be defined by the head, upper arm and neck, where the endpoint of the joint angle coincides with the neck joint and the head and upper arm are non-adjacent body segments. Referring to FIGS. 3A-3B, a joint angle may be defined by the joint center of non-adjacent vertebrae. In the example shown, the joint angle is defined by a joint center located between, for purposes of illustration, a vertebra generally indicated at 17, and a non-adjacent vertebra generally indicated at 18. In the example shown in FIGS. 3A-3B, the non-adjacent vertebra may be, for example, the C1 and T12 vertebrae, respectively. Accordingly, in the FIGS. 3A-3B, the sensing device 16 is configured to measure the movement of non-adjacent body segments 17, 18, and the sensing device 16 is configured such that the triggering mechanism 12 is extended across multiple joints and body segments, including the joint center measured by the joint angle $\theta$ shown in FIGS. 3A-3B corresponding to a first position and a second position of the body 10.

Further, as referred to herein, the term proximal is understood to be defined as located between the reference point and the center of mass of the body, and the term distal is defined as located outward of the reference point relative to the center of mass of the body. For example, a location on the body described as distal of the shoulder joint, using the shoulder joint as the reference point, is a location on the arm, forearm, hand or arm limb generally, e.g., outboard or outward of the shoulder joint with respect to the center of mass of the body. Additionally, for example, a location on the body described as proximal of the shoulder joint, using the shoulder joint as a reference point, is a location on the body which is inward of the shoulder joint, e.g., located on the torso, head, leg, limb or any other body location which is closer to the center of mass of the body than the reference shoulder joint. The sensing device 16 may be configured such that the first covering portion 24 may be positioned in contact with a moving segment 17 and the second covering portion 26 may be positioned in contact with a reference segment 18 wherein the moving segment 17 is one of distal and proximal to the reference segment 18, and/or wherein the moving segment 17 is one of proximal and distal to the joint center 14 located between in segments 17, 18, and the reference segment 18 is the other of proximal and distal to the joint center 14.

Further, as referred to herein, the term contralateral is understood to be defined as located on opposite sides of the body, for example, the left hand is contralateral to the right hand, the right arm is contralateral to the left leg, and the left side of the back is contralateral to the right side of the back.

One or more joints and joint centers may be located between two adjacent or non-adjacent contralateral body segments. For example, the spine joint is located between the right and left sides of the back, which represent adjacent contralateral body segments. Additionally, for example, the neck joint is located between the right hand and left hand, which represent non-adjacent contralateral body segments. The sensing device 16 may be configured such that the first covering portion 24 may be positioned in contact with a moving segment 17 and the second covering portion 26 may be positioned in contact with a reference segment 18 wherein the moving segment 17 may be contralateral to the reference segment 18 and the segments 17, 18 may be one of adjacent and non-adjacent to each other.

For example, a sensing device 16 (not shown) may be configured to measure the movement of adjacent contralateral segments such as the right and left sides of the torso, relative to joints in the spine. In such a configuration, the sensor 19 is attached to a first covering portion 24 of a covering 15 in contact with the right side of the torso and the first end of the triggering mechanism 12 is attached to a second covering portion 26 of a covering 15 in contact with the left side of the torso, such that triggering mechanism 12 extends from a first body segment, the right side of the torso, to a second body segment, the left side of the torso, while extending or crossing over the spine joint 14 therebetween, such that movement of the adjacent contralateral body segments may be measured. The covering 15 may be configured, for example, as a band or sleeve including the first covering portion 24 and the second covering portion 26, the covering 15 configured to surround the torso such that the covering 15 is in contact with the perimeter surface of the torso of the body 10 being measured.

In another example, the sensing device 16 may be configured to measure the movement of non-adjacent contralateral segments such as the right leg and the left leg, relative to the hip joints. In such a configuration, the sensor is attached to a second covering portion 26 of a covering 15 in contact with the right leg and the first end of the triggering mechanism 12 is attached to a first covering portion 24 of the covering 15 in contact with the left leg, such that triggering mechanism 12 extends from a first body segment, the right leg, to a second body segment, the left leg, while extending or crossing over the left and right hip joints therebetween, such that movement of the non-adjacent contralateral body segments may be measured. The covering 15 may be configured, for example, as a pant or trouser which may be worn on the body 10 being measured.

As referred to herein, the term ipsilateral is understood to be defined as located on the same side of the body, for example, the left arm is ipsilateral to the left leg, the right side of the back is ipsilateral to the right arm, the left side of the back is ipsilateral to the left foot. One or more joints and joint centers may be located between two adjacent or non-adjacent ipsilateral body segments. For example, the right shoulder joint is located between the right side of the back and the right arm, which represent adjacent ipsilateral body segments. Additionally, for example, the left hip joint is located between the left leg and left arm, which represent non-adjacent ipsilateral body segments. The sensing device 16 may be configured such that the first covering portion 24 may be positioned in contact with a moving segment 17 and the second covering portion 26 may be positioned in contact with a reference segment 18 wherein the moving segment 17 may be ipsilateral to the reference segment 18 and the segments 17, 18 may be one of adjacent and non-adjacent to each other. For example, the sensing device 16 may be configured to measure the movement of non-adjacent ipsilateral segments such as the left hand, relative to the left arm. In such a configuration, the input interface 11 and sensor 19 is located in a second covering portion 26 of the covering 15 in contact with the left arm and the second attachment point 13 is located in a first covering portion 24 of the covering 15 in contact with the left hand, such that triggering mechanism 12 extends from a reference body segment, the left arm, to a moving body segment, the left hand, while extending or crossing over the left elbow and wrist joints therebetween, such that movement of the non-adjacent ipsilateral body segments may be measured.

In another example, the sensing device 16 may be configured to measure the movement of adjacent ipsilateral segments such as the right side of the torso and the right upper arm, relative to the right shoulder joint, as shown in FIGS. 2A and 2B. In such a configuration, the sensor 19 is attached to a second covering portion 26 of the covering 15 in contact with the right side of the torso, and the first end of the triggering mechanism 12 is attached to a first covering portion 24 of covering 15 in contact with the right upper arm, such that triggering mechanism 12 extends from a reference body segment 18, the right side of the torso, to a moving body segment 17, the right upper arm, while extending or crossing over the shoulder joint 14 therebetween, such that movement of the adjacent ipsilateral body segments may be measured to determine the joint angle θ as shown in FIGS. 2A and 2B. The covering 15, in the non-limiting example shown in FIGS. 2A and 2B, is configured as a garment, which in the present example, is configured as a shirt.

As described previously and illustrated by FIG. 2B, the sensing device 16 may be configured such that the first covering portion 24 may be positioned in contact with a moving segment 17 and the second covering portion 26 may be positioned in contact with a reference segment 18 wherein the moving segment 17 is distal to the joint center 14 and the reference segment 18 is proximal to the joint center 14. As shown in FIG. 2B, the sensing device 16 can be attached to covering 15 such that first end of the triggering mechanism 12 can be placed distal to relative to joint center 14 at attachment 13 and the sensor 19 can be anchored proximal relative to the joint center 14.

In an alternate configuration (not shown), the sensing device 16 may be configured with the orientation of the first end of triggering mechanism 12 and the sensor 19 opposite to the configuration shown in FIG. 2B, such that the first end of the triggering mechanism may be attached to the second portion 26 (referring to FIG. 2B) in contact with the reference body segment 18, and sensor 19 may be attached the first covering portion 24 (referring to FIG. 2B) in contact with the moving segment 17. Thus configured, the sensing device is located distal to the joint center 14, and the triggering mechanism is extended from the moving segment 17 across the joint center 14 to a covering portion in contact with the reference segment 18.

FIGS. 3A and 3B show, as described previously, a sensing device 16 configured to provide an output corresponding to a joint angle θ defined by a vertebra generally indicated at 17, a non-adjacent vertebra generally indicated at 18, and a joint center 14 (see FIG. 3B) located between and defining the apex of the joint angle θ. In the example shown in FIGS. 3A-3B, the non-adjacent vertebra may be, for example, the C1 vertebra (generally indicated at 17) and the T12 vertebra (generally indicated at 18), respectively. Accordingly, in the FIGS. 3A-3B, the sensing device 16 is configured to measure the movement of non-adjacent body segments 17, 18, where the triggering mechanism 12 is extended across multiple joints and body segments, including the joint center measured by the joint angle $\theta_1$ shown in FIG. 3A and corresponding to a first body position and the joint angle $\theta_2$ shown in FIG. 3B and corresponding to a second position of the body 10. The sensing device 16 shown in FIGS. 3A and 3B may be included in a system such as the system 40 shown in FIG. 1. In a non-limiting example, the sensing device 16 may be configured to wirelessly communicate with a remote processor 20 and/or a remote output device 34 such that the sensing device 16 may transfer the output signals from the sensor 19 to the remote processor as the performer moves from a preferred posture, e.g., the first position shown in FIG. 3A to a less desirable posture, e.g., the second position shown in FIG. 3B. The remote processor 20 may, upon detecting movement to the less desirable posture, provide a message to the performer, which may be displayed on the output device 34, to make an adjustment in his posture to the preferred position.

As shown in the non-limiting examples in FIGS. 2A, 3A 3B, 5A, 5B, 6A, 6B, and 6C, the triggering mechanism 12 when actuated by a movement of the movable segment 17 is operatively connected to the input interface 11 such that the force input produced by the triggering mechanism 12 is inputted directly to the sensor 19. As discussed previously, and as shown in FIGS. 4A, 4B, 4C, 4D, 7A, 8A, and 8B, an intermediate device 22 may be interposed between the input interface 11 of the sensor 19 and the triggering mechanism 12, such that the activation of the intermediate mechanism 22 generates an input force to the interface 11 and the sensor 19. The intermediate mechanism 22 may be configured to filter or isolate the input force generated by the triggering mechanism 12 in response to a activating movement of the movable member 17 from the sensor 19 when the input force generated by the triggering mechanism 12 does not meet a threshold input force predetermined for the sensing device 16, and/or the corresponding movement does not meet a threshold level predetermined for the sensing device 16. Such a configuration provides the advantage of preventing inadvertent or non-intentional inputs to the sensor 19, which may cause noise in the signal data logged, and/or provides a filter to segment the output signals, e.g., to truncate the distribution of the unfiltered output signals to focus monitoring and analysis in a target range of movement. As used herein, "unfiltered output signals" refer to the population of output signals which would be generated by a sensing device 16 configured without an intermediate mechanism 22.

Various configurations of an intermediate mechanism 22 are possible, and the examples shown and described herein are intended to be non-limiting. As shown in a first example configuration in FIG. 4A, the intermediate mechanism 22 may be configured as a cam 22 in selective contact with a sensor contact 44 and operatively connected to the first end of the triggering mechanism 12 at attachment 42. In the example shown in FIG. 4A, the sensor contact 44 is configured as a cam follower, and the input interface 11 is defined by the contact profile between the surfaces of the cam 22 and the cam follower 44, where increasing interference between the surfaces causes an upward deflection of the cam follower 44 (as illustrated in the drawing) in the direction w, and decreased interference between the surfaces causes decreased or little to no deflection of the cam follower 44. As shown in FIG. 4A, when the triggering mechanism 12 is initially activated by a movement of a movable joint 17, the triggering mechanism 12 exerts a tensile force at attachment 42 in a direction X on the cam 22, causing the cam 22 to rotate in a direction $\omega$. The cam 22 is configured such that the surface of the cam rotates away from the surface of the cam follower 44, decreasing the pressure exerted by the cam 22 on the cam follower 44, thereby decreasing the deflection of the cam follower 44 and isolating and/or filtering the sensor 19 from the input force generated by the triggering mechanism 12. As the input force generated by the triggering mechanism 12 increases above a threshold level, the cam 22 is further rotated in a direction $\omega$ such that the base circle portion of the cam 22 contacts the cam follower, increasing the pressure on the cam follower and causing it to deflect upward (as oriented on the drawing page). The upward deflection provides an actuating force through interface 11 and the cam follower 44 to the sensor 19, causing the sensor 19 to generate an output signal corresponding to the input force of the triggering mechanism 12 and the activating movement of the moving segment 17.

In another configuration shown in FIG. 4B, the intermediate mechanism 22 may be configured as a reel or spool 22 including a contact element 46 which may be selectively rotated in selective contact with the input interface 11 of a sensor contact 44. The reel 22 is operatively connected to the first end of the triggering mechanism 12, wherein a length or portion of the triggering mechanism may be wrapped around the axis of the reel 22, such that the triggering mechanism 12 may be activated to exert a tensile force in a direction X below a threshold level without causing sufficient rotation of the reel 22 and the contact element 46 in a direction w, such that below a threshold level the contact element 46 exerts minimal to no pressure against the input interface 11. In the example shown in FIG. 4A, the sensor contact 44 may be configured as a pressure transducer, for example, such that rotation of the contact element 46 in contact with and against the input interface 11 may exert a pressure on the pressure transducer 44, thereby causing the pressure transducer 44 to actuate the sensor 19 to generate an output signal. As shown in FIG. 4A, when the triggering mechanism 12 is initially activated by a movement of a movable joint 17, the triggering mechanism 12 exerts a tensile force in the direction X, which initially takes up any slack in the triggering mechanism 12 where it is wrapped around and/or attached to the axis of the reel 22. As the tensile force exerted by the triggering mechanism increases, the reel 22 and the contact element 46 attached thereto rotate in a direction w. When the tensile force exerted by the triggering mechanism 12 reaches a threshold level, the reel 22 and the contact element 46 are sufficiently rotated such that the contact element 46 makes contact with the input interface 11 of the pressure transducer 44, actuating the sensor to generate an output signal corresponding to the input force of the triggering mechanism 12 and the activating movement of the moving segment 17.

In another configuration shown in FIG. 4C, the intermediate mechanism 22 may be configured as a connector 42 including a secondary triggering mechanism 38, which may also be referred to herein as a secondary mechanism. The first end of the triggering mechanism 12 is operatively connected to the connector 42, and a first end of a secondary mechanism 38 is operatively connected to the input interface 11 of the sensor 19. The connector 42 may be of any configuration suitable to operatively connect the triggering mechanism 12 to the secondary mechanism 38. In a non-limiting example, the secondary mechanism 38 may be configured of a material having a higher spring coefficient than the spring coefficient of the triggering mechanism 12, such that the secondary mechanism 38 will filter and/or isolate the tensile input force of the triggering mechanism 12 until a predetermined threshold is reached. The secondary mechanism 38 may comprise an elastic material, a spring, a spring-like element, or another configuration or material providing the higher spring coefficient. As shown in FIG. 4C and described herein, below a threshold level the tensile force exerted by the triggering mechanism 12 in a direction X is insufficient to activate (extend) the secondary mechanism 38 sufficiently to transfer an input force to the input interface 11 of the sensor 11. When the tensile force exerted by the triggering mechanism 12 reaches or exceeds the predetermined threshold level, the triggering mechanism 12 exerts sufficient force to cause the secondary mechanism 38 to exert an input force on the sensor 19, thereby actuating the sensor to generate an output signal corresponding to the input force of the triggering mechanism 12 and the activating movement of the moving segment 17.

In a non-limiting example, FIGS. 7A, 8A and 8B show an intermediate mechanism 22A configured similarly to the configuration of the intermediate mechanism 22 described for FIG. 4C, and as an optional construction of the sensing device 16A shown in FIG. 7A. The intermediate mechanism 22A includes a secondary mechanism 38A configured as a spring attached at one end to the input interface 11A of the sensor 19A and at the other end to a connector 42A configured as a loop through which the triggering mechanism 12A is passed, such that the triggering mechanism 12A, when extended, exerts a tensile force on the loop 42A and the spring 38A. The intermediate mechanism 22A operates as described for FIG. 4C, however the loop 42A provides an additional isolating and/or filtering feature. As the triggering mechanism 12A is extended in response to an increase in the joint angle θA, the triggering mechanism 12A may extend in length before contacting, e.g., interfering with, the loop 42A to begin to exert a tensile force on the secondary mechanism 22A, thereby isolating the input force exerted by the triggering mechanism 12A from the spring element 38A and the sensor 19A.

Referring now to FIG. 8A, the intermediate mechanism 22A is shown in a simplified configuration, where the intermediate mechanism 22A is configured as a loop operatively connected to the sensor 19A, such that the loop 22A defines the input interface 11A. As previously described for FIG. 7A, the triggering mechanism 12A which is passed through the loop 22A may extend in length before contacting and meeting sufficient resistance from the loop 22A to exert an input force above a threshold level. Accordingly, until the triggering mechanism 12A engages the loop 22A in resistive contact, the loop 22A effectively isolates and/or filters the sensor 19A from an input force below the threshold level. When the triggering mechanism 12A is extended sufficient due to the activating movement of the segments 17A, 18A (see FIG. 7A) to exert a tensile force on the loop 22A, the tensile force may be transferred via the loop 22A to the input interface 11A of the sensor 19A, the triggering mechanism 12A actuating the sensor to generate an output signal corresponding to the input force of the triggering mechanism 12A and the activating relative movement of the segment 17A, 18A (see FIG. 7A).

Referring now to FIG. 4D, another non-limiting example configuration of an intermediate mechanism is shown. The intermediate mechanism 22 may be configured as a frictional element 22 slidable engaged with an input interface 11 of the connector 22, such that sliding displacement of the frictional element 22 in a direction X produces an actuating input to the input interface 11. The frictional element 22 is operatively connected to a first end of the triggering mechanism 12 at attachment 42. The intermediate mechanism is configured such that the frictional force f at the input interface 11 which must be overcome prior to initiating sliding movement and displacement of the frictional element 22 from its initial position is greater than the input force exerted by the triggering mechanism 12 below a predetermined threshold level. As shown in FIG. 4D and described herein, below a threshold level the tensile force exerted by the triggering mechanism 12 in a direction $X_1$ is insufficient to overcome the frictional force f resisting the sliding movement of the friction element 22 in a direction $X_2$, such that the friction element 22 is not displace in a direction $X_2$ and the input force exerted by the triggering mechanism 12 below the threshold level is isolated from the sensor 19. When the tensile force exerted by the triggering mechanism 12 reaches or exceeds the predetermined threshold level, e.g., reaches a sufficient input force to overcome the frictional resistance f between the frictional element 22 and the interface 11, the frictional element 22 is displaced in a direction $X_2$ proportional to the magnitude of the input force exceeding the threshold level. The displacement of the frictional element 22 relative to the interface 11 actuates the sensor to generate an output signal corresponding to the input force of the triggering mechanism 12 and the activating movement of the moving segment 17.

The configurations shown in FIGS. 4A, 4B, 4C, 4D, 7A, 8A and 8B are not intended to be limiting. Alternative methods and materials not shown but within the scope of the sensing device described herein can be used to convert a tensile load of the triggering mechanism 12 to an actuation or perturbation of the sensor. For example, conductive threads may be integrated in the covering 15 and configured to provide an intermediate mechanism 22. Other cam-type mechanisms or mechanical mechanisms may be used as a force transferring mechanism 22 to transfer the force load of the triggering mechanism 12 to actuate the sensor 19. Not shown, but understood, an intermediate mechanism 22 may be configured to isolate the sensor 19 from input loads above a maximum level, for example, to protect the sensor from overloading. The configurations as described herein or other configurations including, for example, cams, secondary mechanisms, disconnect features or mechanically biased features may be modified or adapted, for example, to filter or isolate potentially damaging or aberrant loads from actuating the sensor 19.

FIGS. 5A, 5B, 6A, 6B, 6C, 7A, 7B, 8A, 8B, 9, and 10 show non-limiting examples of a sensing device 16 configured for the measurement of movements of various joint and segment configurations. The sensing devices 16 illustrated in FIGS. 5A, 5B, 6A, 6B, 6C, 7A, 7B, 8A, 8B, 9, and 10 are configured to operate substantially similar to sensing devices 16 as previously described.

In a non-limiting example, FIG. 5A shows a sensing device 16 configured to measure the movement of adjacent ipsilateral segments 17, 18, shown as the upper leg 18 and the lower leg 17, relative to the knee joint 14. In the configuration shown, the sensor 19 is attached to a second covering portion 26 of a covering 15 in contact with the upper leg segment 18 and the first end of the triggering mechanism 12 is attached to a first covering portion 24 of the covering 15 in contact with the lower leg segment 17, such that triggering mechanism 12 extends from a reference segment 18, the upper leg, to a moving body segment, the lower leg, while extending or crossing over the posterior surface of the knee joint therebetween, such that movement of the adjacent ipsilateral body segments 17, 18, including a joint angle θ defined by the segments 17,18 and having its origin coincident with the joint center 14, may be measured. The covering 15 may be configured, as in the example shown, as a sleeve which may be slidably positioned in contact with knee joint 14 and the upper and lower leg portions adjacent to the knee joint 14. The triggering mechanism 12 may be extended along an external surface of the sleeve 15 or may be integrated into the sleeve 15 in a manner which does not constrain activation of the triggering mechanism in response to a movement of the movable segment 17.

In another non-limiting example, FIG. 5B shows a sensing device 16 configured to measure the movement of the upper leg 18 and the lower leg 17, relative to the knee joint 14. In the configuration shown, the sensor 19 is attached to a second covering portion 26 of a covering 15 in contact with the upper leg segment 18 and the first end of the triggering mechanism 12 is attached to a first covering portion 24 of the covering 15 in contact with the lower leg segment 17, such that triggering mechanism 12 extends from a reference segment 18, the upper leg, to a moving body segment, the lower leg, while extending or crossing the posterior of the knee joint therebetween, such that movement of the adjacent ipsilateral body segments 17, 18, including a joint angle θ defined by the segments 17,18 and having its origin coincident with the joint center 14, may be measured. The covering 15 may be configured, as in the example shown, as a sleeve which may be slidably positioned in contact with knee joint 14 and the upper and lower leg portions adjacent to the knee joint 14. The triggering mechanism 12 is extended from an external surface of the first covering portion 24 to the sensor 19 attached to the second covering portion 26, such that the triggering mechanism is generally not in contact with the surface of sleeve 15 for joint angles less than 180 degrees.

FIGS. 6A and 6B show a sensing device 16 configured to measure the translation of the knee joint 14 with respect to the upper leg segment 18 and the lower leg lower leg segment 17. In the configuration shown, the covering 15 of the sensing device 16 is oriented in contact with the knee joint 14 and the upper and lower leg portions adjacent to the knee joint 14, such that the sensor 19 is attached to a second covering portion 26 of a covering 15 in contact with a lateral surface of the upper leg segment 18 and the first end of the triggering mechanism 12 is attached to a first covering portion 24 of the covering 15 in contact with a lateral surface of the lower leg segment 17, such that triggering mechanism 12 extends from a reference segment 18, the upper leg, to a moving body segment 17, the lower leg, while extending or crossing laterally over the knee joint 14 therebetween. When the adjacent ipsilateral body segments 17, 18 are translated relative to each other by exerting a force $F_1$ shown in FIG. 6A and/or a force $F_2$ shown in FIG. 6B, the triggering mechanism 12 changes in length thereby changing the input force exerted on the sensor 19, such that the translation distance may be measured.

FIG. 6C shows a sensing device 16 configured to measure the translation of the knee joint 14 with respect to the upper leg segment 18 and the lower leg lower leg segment 17, when a force F is exerted on the joint 14. In the configuration shown, the covering 15 of the sensing device 16 is oriented in contact with the knee joint 14 and the upper and lower leg portions adjacent to the knee joint 14, such that the sensor 19 is attached to a second covering portion 26 of a covering 15 in contact with a medial surface of the upper leg segment 18 and the first end of the triggering mechanism 12 is attached to a first covering portion 24 of the covering 15 in contact with a medial surface of the lower leg segment 17, such that triggering mechanism 12 extends from a reference segment 18, the upper leg, to a moving body segment 17, the lower leg, while extending or crossing laterally over the knee joint 14 therebetween. When a force F is exerted on the moving segments the triggering mechanism 12 exerts a tensile force on the input interface 11 of the sensor 19, thereby actuating the sensor to generate an output signal corresponding to the translation distance of the knee joint. The first covering portion 24 and the second covering portion 26 in the non-limiting example shown are each configured as a band or strap, which may be, for example, an elasticized band slidably positioned in contact with the leg segment, or may be, for example, configured with a one or more fasteners, which may be adjustable fasteners, such as hook and eye fasteners, such that the covering portion may be wrapped around the body segment and adjustably fastened in contact with the appropriate surface of the respective body segment.

As shown in FIGS. 7A and 7B, more than one sensing device 16 may be positioned in contact with a moving body portion, to facilitate concurrent measurement of the movement of more than one combination of body segments. As shown in FIGS. 7A and 7B, a first sensing device 16A is positioned over a first joint center 14A and a second sensing device 16B is positioned over a second joint center 14B. This configuration may provide improvements in testing efficiency, where more than one test sharing a similar movement pattern may be conducted concurrently, or testing set-up time may be decreased by positioning more than one sensing device 16A, 16B on the wearer in a single session. Concurrent testing using more than one sensing device 16A 16B may be required to correlate measurements of movements obtained from the different sensing devices 16A 16B, or to analyze for interactions in the movement patterns measured by each sensing device 16A, 16B. Not shown but understood, the multiple sensors 19A, 19B may each be configured to transmit output signals to a shared processor 20 to a shared memory device, wherein the processor and/or the memory device may be located on one of the coverings, such as the covering 15A, or which may be located remotely, for example, where the sensing devices 16A, 16B and the remote processor 20 and/or memory device may be configured for wireless communication.

FIGS. 7A and 7B show the first sensing device 16A configured to measure the movement of non-adjacent segments relative to a non-adjacent joint center 14A, where the first sensing device 16A is configured such that the sensor 19A is positioned over the joint center 14A, which may be, for example, a joint located between two carpal bones. The triggering mechanism 12A is operatively attached to the first and second body segments, e.g., to the metacarpal of the thumb and the phalange of the index finger, at respective attachments 13A and $13A_2$ and to a connector 22A, through which the triggering mechanism 12A exerts an input load on the sensor 19A. As described previously, the connector 22A may be configured as an intermediate mechanism 22A configured to isolate and/or filter input forces from the sensor 10 where the input force exerted on the connector 22A does not meet a predetermined threshold or condition. As is shown in FIG. 7A, as the thumb moves away from the metatarsal and/or the proximal phalange of the index finger, the joint angle $θ_A$ increases between the body segments 17A, 18A and the triggering mechanism 12A is extended, such that the triggering mechanism 12A may exert a tensile force on the connector 22A which may be transferred as a force input to the input interface 11A of the sensor 19A. The sensor 19A, when actuated by the tensile force input, may generate an output signal corresponding to the measured change in the joint angle $θ_A$. The covering 15A is configured, in a non-limiting example, as a portion of a glove, which may be slidably positioned over the index finger, the thumb and the wrist. Other configurations of the covering 15A of the sensing device 16A are possible, and may include one or more covering portions which may be configured to as a band, sleeve or strap slidably positioned or adjustably fastened to the appropriate position on a finger or wrist portion, or may be configured as a pad or patch, for example, which may be positioned in contact with the appropriate position for example, with an adhesive or other removable fastener.

FIGS. 7A and 7B show a second sensing device 16B configured to measure the movement of adjacent phalange segments 17B, 18B relative to a knuckle joint located therebetween, in an individual finger. As shown in FIG. 7A, the moving segment 17B is shown as the intermediate phalange of the finger commonly referred to as the ring finger, and the reference segment 18B is shown as the proximal phalange of the ring finger. The first end of the triggering mechanism 12B is operatively attached to a first covering portion 24B at 13B and the second end of the triggering mechanism 12B is operatively connected to the sensor 19B at an input interface 11B. The sensor 19B is operatively attached to a second covering portion 26B. The covering portions 24B and 26B, as shown in the non-limiting example of FIG. 7A, may be configured as adhesive patches which may be positioned in contact with the respective segments 17B, 18B. Alternatively, the covering portions 24B, 26B may be configured as shown in FIG. 9, as generally annular shaped elements, such as rings, bands or straps, which may be slide onto the finger or adjustably fastener thereon. The covering portions 24B, 26B may be configured as portions of a sleeve (not shown) or a glove or glove portion, or in any other configuration which may be positioned over the phalange segments 17B, 18B to position the sensing device 16B such that the triggering mechanism 12B may be extended to cross over the anterior surface of the knuckle joint 14B. As shown in FIG. 7B, movement of the phalange segments 17B, 18B from a first position to a second position activates the triggering mechanism 12B to provide an input force to the sensor 19B, thereby actuating the sensor 19B to generate an output signal corresponding to a measurement of the movement of the segments 17B, 18B relative to the joint 14B. For example, the segments 17B, 18B may be moved from a first position corresponding to a joint angle $\theta_{B1}$ to a second position corresponding to a joint angle $\theta_{B2}$ as shown in FIG. 7B.

FIG. 9 shows sensing device 16C which illustrates an alternative configuration for the sensing device 16A shown in FIG. 7A. As shown in FIG. 9, a triggering mechanism 12C is extended between an attachment 13C to a first covering portion 24C and an input interface 11C of a sensor 19C operatively attached to a second covering portion 26C. The sensing device 16C is configured to measure the same joint angle $\theta_A$. As the thumb moves away from the metacarpal and/or the proximal phalange of the index finger, the joint angle $\theta_A$ increases and the triggering mechanism 12C is extended to exert a tensile input force on the sensor 19C, actuating the sensor 19C to generate an output signal corresponding to the joint angle $\theta_A$.

In another non-limiting example, FIG. 10 shows a sensing device 16D including a plurality of triggering mechanisms 12 including triggering mechanisms $12D_1$, $12D_2$, $12D_3$, and a plurality of second attachment portions 13 including second attachment portions $13D_1$, $13D_2$, $13D_3$. Each of the triggering mechanisms $12D_1$, $12D_2$, $12D_3$ is configured to provide an input force to a shared sensor 19D. The covering 15 is configured as a glove 15D, and each of the triggering mechanisms $12D_1$, $12D_2$, $12D_3$ is configured to measure the movement of non-adjacent segments of the hand, where each respective first end of each of the triggering mechanisms $12D_1$, $12D_2$, $12D_3$ is operatively attached at a respective second attachment portion $13D_1$, $13D_2$, $13D_3$ to a respective distal phalange of the digits commonly referred to, respectively, as the thumb, index finger and ring finger, and where the second end of each of the triggering mechanisms $12D_1$, $12D_2$, $12D_3$ is operatively connected to the sensor 19D positioned in contact with the carpals, e.g., the wrist. As shown in FIG. 10, each of the thumb, index finger and ring finger includes a joint center 14, shown respectively in FIG. 10 as joint centers $14D_1$, $14D_2$, $14D_3$. Each of the triggering mechanisms $12D_1$, $12D_2$, $12D_3$ extends and/or crosses over a respective joint center $14D_1$, $14D_2$, $14D_3$, generally indicated as the joint center corresponding to the joint between the metacarpal and the proximate phalange of the respective digit. The sensing device 16D configured as shown in FIG. 10 may provide the opportunity to correlate and/or identify patterns in the movements of multiple digits measured during various hand movements.

It would be understood that a sensing device such as sensing device 16 may be configured in a covering to measuring many different intra-limb, inter-limb and/or joint movements including combinations of various body segments and joints. Further, a covering may be instrumented with a plurality of sensing devices such that movements of multiple body segment and joint combinations can be measured simultaneously. The output signals from the plurality of sensing devices may be recorded, collected and/or analyzed using circuitry and memory storage which may be included in a device incorporated into the covering. Additionally, a sensing device of plurality of sensing devices may be configured to transmit measurement data and signals using wireless methods such that the data collection, recording or memory storage device may be located remotely from the covering and/or wearer of the covering.

The use of a covering instrumented with a sensing device to measure the movement of a segment, limb or joint presents numerous advantages, including low cost, unobtrusive use, easy monitoring and flexible configurations for use in measuring multiple joints. The method, apparatus and system described herein may be configured for measuring intra-limb, inter-limb and/or joint movements, and may be configured for use related to any joint in the body, between any two adjacent or non-adjacent body segments and may include individual joints or combinations of joints including but not limited to the shoulder, elbow, wrist, trunk, neck, hip, knee, ankle, and/or joints contained in the hand and foot. Other configurations of the sensing device and system described herein are possible, and the figures and descriptions provided herein are not intended to be limiting. For example, the sensing device and/or system described herein is not limited to measurement of a human body, but may be applied to other moving bodies, which may include non-human living bodies or other non-living moving or animated bodies, such as a body which is moved by electro-mechanical or mechanical means, for the measurement of movement thereof.

While the best modes for carrying out the invention have been described in detail, those familiar with the art to which this invention relates will recognize various alternative designs and embodiments for practicing the invention within the scope of the appended claims.

What is claimed is:
1. A sensing device comprising:
a sensor operatively attachable to a covering;

a triggering mechanism operatively attachable at a first end to the covering and operatively connected at a second end to the sensor;

wherein the covering includes first and second covering portions and is positionable on a body such that the first covering portion is in contact with a first segment of the body and the second covering portion is positioned in contact with a second segment of the body;

wherein, when the sensing device is attached to the covering and the covering is positioned in contact with the body:
- one of the sensor and the first end is attached to one of the first and second covering portions,
- the other of the sensor and the first end is attached to the other of the first and second covering portions, and
- the triggering mechanism extends from the first segment to the second segment, such that movement of one of the first and second segments activates the triggering mechanism to provide an input to the sensor; and wherein the input actuates the sensor to generate an output defined by the movement.

2. The sensing device of claim 1, further including:
a removable storage device;
wherein the output from the sensor is received by and stored on the removable storage device.

3. The sensing device of claim 1, further comprising:
an output device configured to receive the output from the sensor in real time.

4. The sensing device of claim 1, further including:
a preceding mechanism, wherein the preceding mechanism is operatively connected to at least one of the triggering mechanism and the sensor; and
wherein the sensing device is configured such that the preceding mechanism must be activated prior to at least one of activating the triggering mechanism to provide the input and actuating the sensor to generate the output.

5. The sensing device of claim 1, wherein:
the triggering mechanism is a first triggering mechanism;
the sensor is configured to output a first signal and at least another signal;
the sensing device further comprising:
at least one other triggering mechanism operatively attachable at a first end to the covering and operatively connected at a second end to the sensor;
wherein activating the at least one other triggering mechanism provides at least one other input to the sensor; and
wherein the sensor is actuated by the at least one other input to generate at least one other output.

6. The sensing device of claim 1, wherein the sensor is configured to output a first signal and a second signal;
wherein the first signal is defined by the input received from the triggering mechanism; and
wherein the second signal is defined independently of the input received from the triggering mechanism.

7. The sensing device of claim 1, further comprising:
an output device configured to receive the output from the sensor;
wherein the output device includes a display element; and
wherein the output device is operable to display information defined by the output, via the display element.

8. The sensing device of claim 7, wherein the information includes at least one of a measurement of the movement, a count of movement repetitions, an analysis of a movement, a comparison of the movement to a movement threshold, a message defined by the output, and an alert defined by the output.

9. The sensing device of claim 1, further including:
an intermediate mechanism operatively attached to the second end of the triggering mechanism and in selective communication with the sensor, such that movement of one of the first and second segments activates the triggering mechanism to provide the input to the intermediate mechanism.

10. The sensing device of claim 9, wherein the intermediate mechanism is configured to transfer the input to the sensor when the input meets a predetermined threshold, and to isolate the input from the sensor when the input does not meet the predetermined threshold.

11. The sensing device of claim 1, wherein the sensing device is configured for wireless communication with an output device such that information can be transferred wirelessly between the sensing device and the output device;
wherein the information comprises the output.

12. The sensing device of claim 11, wherein the output device is located remotely from the sensing device and the covering.

13. The sensing device of claim 12, wherein the output device is attachable to the body.

14. The sensing device of claim 12, wherein the output device is configured to receive the output from the sensor and at least one of store the output in a memory and transmit the output to a computing device.

15. A system for measuring movement of a first segment of a body relative to a second segment of the body, the system comprising:
a sensing device comprising:
    a sensor operatively attachable to a covering;
    a triggering mechanism operatively attachable at a first end to the covering defining first and second covering portions; and
    the triggering mechanism operatively connected at a second end to the sensor;
wherein the covering is positionable on a body such that the first covering portion is in contact with a first segment of the body and the second covering portion is positioned in contact with a second segment of the body;
wherein, when the sensing device is attached to the covering and the covering is positioned in contact with the body:
    one of the sensor and the first end is attached to one of the first and second covering portions,
    the other of the sensor and the first end is attached to the other of the first and second covering portions, and
    the triggering mechanism extends from the first segment to the second segment,
such that movement of one of the first and second segments activates the triggering mechanism to provide an input to the sensor; and
wherein the input actuates the sensor to generate an output defined by the movement.

16. The system of claim 15, further comprising:
an output device configured to receive the output from the sensor and to generate a measurement of the movement corresponding to the output.

17. The system of claim 15, further comprising:
an output device configured to receive the output and wirelessly transmit the output for storage in a memory;
wherein the memory is remote from the output device.

18. The system of claim 15, further comprising at least one other sensing device operatively attachable to the covering and actuable to generate at least one other output.

19. The system of claim 15, further comprising at least one other triggering mechanism operatively attachable at a first end to the covering and operatively connected at a second end to the sensor;
wherein activation of the at least one other triggering mechanism provide at least one other input to the sensor.

20. The system of claim 15, further comprising:
a computing device in communication with the sensing device such that information can be transferred between the computing device and the sensing device;
wherein the computing device is configured to:
receive the output from the sensing device; and
analyze at least one of the output and a measurement of movement defined by the output to determine at least one of:
a pattern of movement;
a count of repetitions of movement; and
a message defined by at least one of the output, the measurement of movement, the pattern, and the count.

21. The system of claim 20, wherein the computing device is attachable to the body.

22. The system of claim 20, further comprising:
at least one other sensor configured to generate a signal;
wherein the computing device is configured to:
receive the signal from the at least one other sensor; and
analyze the signal in combination with at least one of the output and the measurement of movement defined by the output to classify the movement.

23. A method comprising:
attaching a sensing device to a covering having first and second covering portions;
wherein the covering is positionable in contact with a body such that the first covering portion is in contact with a first segment of the body and the second covering portion is in contact with a second segment of the body;
wherein the sensing device comprises:
a sensor operatively attachable to the covering defining first and second covering portions;
a triggering mechanism operatively attachable at a first end to the covering; and
the triggering mechanism operatively connected at a second end to the sensor;
wherein the covering is positionable on a body such that the first covering portion is in contact with a first segment of the body and the second covering portion is positioned in contact with a second segment of the body;
attaching one of the sensor and the first end to one of the first and second covering portions;
attaching the other of the sensor and the first end to the other of the first and second covering portions, such that, when the covering is positioned in contact with the body, the triggering mechanism extends from the first segment to the second segment; and
wherein movement of one of the first and second segments of the body activates the triggering mechanism to provide an input to the sensor.

24. The method of claim 23, further comprising:
activating the triggering mechanism to provide the input to the sensor;
wherein the input is defined by the movement of one of the first and second segments;
receiving the input via the sensor; and
generating, via the sensor, an output corresponding to the input.

25. The method of claim 23, further comprising:
receiving, via a computing device, the output from the sensing device; and
analyzing at least one of the output and a measurement of movement defined by the output to determine at least one of:
a pattern of movement;
a count of repetitions of movement; and
a message defined by at least one of the output, the measurement of movement, the pattern, and the count.

* * * * *